(12) United States Patent
Glynn et al.

(10) Patent No.: US 8,627,823 B2
(45) Date of Patent: Jan. 14, 2014

(54) PLEATED BAG FOR INTERVENTIONAL PULLBACK SYSTEMS

(71) Applicant: Volcano Corporation, San Diego, CA (US)

(72) Inventors: Timothy Kevin Glynn, San Marco, CA (US); Ernest W. Heflin, Pleasanton, CA (US); Norman Hugh Hossack, Folsom, CA (US); Julie Ann Riolo, Sacramento, CA (US); Blair D. Walker, Mission Viejo, CA (US)

(73) Assignee: Volcano Corporation, San Diego, CA (US)

( * ) Notice: Subject to any disclaimer, the term of this patent is extended or adjusted under 35 U.S.C. 154(b) by 0 days.

(21) Appl. No.: 13/914,196

(22) Filed: Jun. 10, 2013

(65) Prior Publication Data

US 2013/0274609 A1    Oct. 17, 2013

Related U.S. Application Data

(63) Continuation of application No. 13/361,674, filed on Jan. 30, 2012, now Pat. No. 8,459,266, which is a continuation of application No. 11/453,441, filed on Jun. 14, 2006, now Pat. No. 8,104,479.

(60) Provisional application No. 60/693,743, filed on Jun. 23, 2005.

(51) Int. Cl.
| | |
|---|---|
| *A61B 19/08* | (2006.01) |
| *A61B 19/00* | (2006.01) |
| *A61B 8/14* | (2006.01) |
| *A61F 11/00* | (2006.01) |

(52) U.S. Cl.
USPC ............ 128/853; 600/467; 606/108; 128/898

(58) Field of Classification Search
USPC ......... 128/845, 846, 849, 850, 852, 853, 854, 128/898; 606/108; 600/466, 467
See application file for complete search history.

(56) References Cited

U.S. PATENT DOCUMENTS

| | | |
|---|---|---|
| 2,915,063 A | 12/1959 | Cutter |
| 3,030,957 A | 4/1962 | Melges |
| 4,745,915 A | 5/1988 | Enright et al. |
| 4,905,710 A | 3/1990 | Jones |
| 5,080,108 A | 1/1992 | Roth |
| 5,098,125 A | 3/1992 | Thornton et al. |
| 5,237,984 A | 8/1993 | Williams et al. |

(Continued)

OTHER PUBLICATIONS

United States Patent Office, Notification of Transmittal of the International Search Report and the Written Opinion of the International Searching Authority, or the Declaration for International Application No. PCT/US06/23736, dated Feb. 16, 2007, 6 pages.

*Primary Examiner* — Kevin C Sirmons
*Assistant Examiner* — William Carpenter
(74) *Attorney, Agent, or Firm* — Haynes and Boone, LLP

(57) ABSTRACT

The present invention provides for pleated bags used with interventional pullback systems, including imaging catheters such as IVUS catheters, as well as for use with other catheters. An exemplary pleated bag of the present invention may be an elongate, sterile bag, having a plurality of pleats near the distal end, and including an orifice proximal to the pleats designed to allow passage of a catheter into the bag. The present invention also provides for a system that includes a pullback device, catheter, and pleated bag. The present invention allows for improved imaging catheter procedures at reduced costs.

20 Claims, 20 Drawing Sheets

(56) References Cited

U.S. PATENT DOCUMENTS

| | | |
|---|---|---|
| 5,274,500 A | 12/1993 | Dunn |
| 5,361,781 A | 11/1994 | Antonini |
| 5,433,221 A | 7/1995 | Adair |
| 5,490,524 A | 2/1996 | Williams et al. |
| 5,496,259 A | 3/1996 | Perkins |
| 5,732,712 A | 3/1998 | Adair |
| 5,827,313 A | 10/1998 | Ream |
| 5,876,328 A | 3/1999 | Fox et al. |
| 5,893,833 A | 4/1999 | Pompei et al. |
| 6,269,815 B1 | 8/2001 | Jascomb |
| 6,292,681 B1 | 9/2001 | Moore |
| 6,309,358 B1 | 10/2001 | Okubo |
| 6,974,465 B2 | 12/2005 | Belef et al. |
| 7,044,132 B2 | 5/2006 | Masini |
| 2002/0133058 A1 | 9/2002 | Calderwood |
| 2002/0183723 A1 | 12/2002 | Belef et al. |
| 2006/0177161 A1 | 8/2006 | Turvey |
| 2006/0235436 A1 | 10/2006 | Anderson et al. |

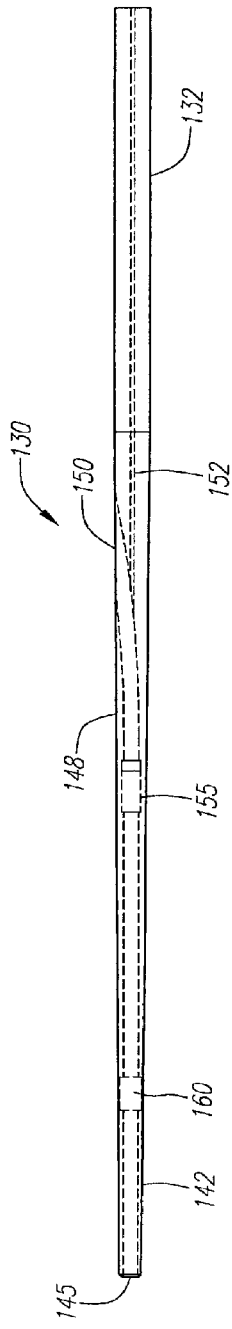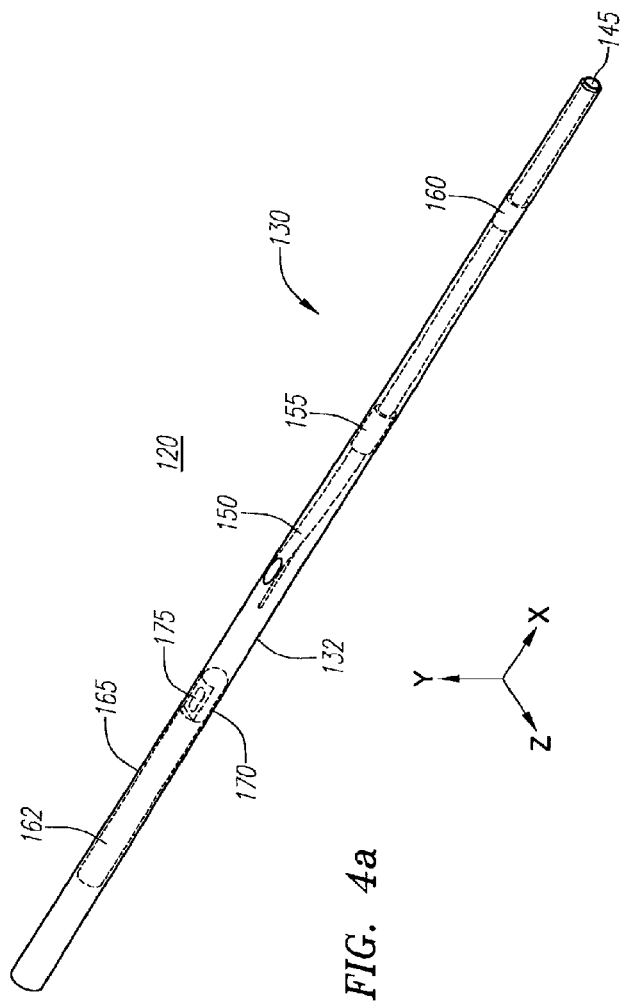
FIG. 4
FIG. 4a

PLEATED BAG FOR INTERVENTIONAL PULLBACK SYSTEMS

CROSS-REFERENCE TO RELATED APPLICATIONS

This application is a continuation of U.S. patent application Ser. No. 13/361,674, filed Jan. 30, 2012, now U.S. Pat. No. 8,459,266, which is a continuation of U.S. patent application Ser. No. 11/453,441, filed Jun. 14, 2006, now U.S. Pat. No. 8,104,479, which claims the benefit of U.S. Provisional Application No. 60/693,743, filed Jun. 23, 2005, each of which is expressly incorporated by reference in its entirety.

BACKGROUND OF THE INVENTION

Most catheters used in interventional medicine are sterile, single-use products, which are disposed after the procedure. Catheters are inserted intraluminally, including intravascular and non-intravascular placement. Catheters can also be inserted interstitially. Many catheters used for diagnosis or treatment, are designed to be used over a range of axial insertion depths. Usually the distal end of the catheter contains a diagnostic or therapeutic element that needs to be placed in the desired target area. Oftentimes, the target area in the body is longer than the diagnostic or therapeutic element, and so the catheter needs to be moved along the target area, so that the entire area can be either diagnosed or treated. For example, in intravascular ultrasound (IVUS), a catheter with one or more ultrasonic transducers at its tip is gradually pulled back along the length of a blood vessel or vascular structure in order to produce an ultrasonic image of the vessel and its disease.

In some applications catheters are pulled or pushed by means of pullback devices. These devices are usually attached to the proximal end of the catheter that extends out of the patient. The devices have a motor that serves to move the catheter at a steady rate in the desired longitudinal direction. This in turn moves the distal element of the catheter through the desired range in the target area. Because the pullback devices have motors and other relatively expensive mechanical and electrical components, they are often constructed and supplied as non-sterile, reusable devices. These devices usually need to be close to the patient, so it is often desirable to place them on the sterile field, for example, on top of the patient's legs or between the patient's legs. In order to place these devices in the sterile field, they are typically covered with a low cost, sterile clear bag, which allows manipulation of the buttons and visualization of the controls. Polyethylene is a common material used, due to its lost cost, transparency and sufficient strength at low wall thickness.

In the past, some IVUS pullback devices have consisted of two main parts, a motor drive and a sled. These parts are separable from each other, and are attached together prior to use. For example, in Cardiovascular Imaging Systems 510(k) #K933517, dated Jul. 16, 1993, the motor drive has a separate motor for rotating a drive shaft containing an ultrasonic transducer at the tip. The sled has its own longitudinal drive motor. In this device, known commercially as the Boston Scientific ClearView pullback device, two sterile bags are used, one to cover the motor drive and one to cover the sled. After attaching the two covered parts to each other, the entire assembly can be placed on the sterile field. In use, the bag that covers the sled is forced to bunch up, due to the translation between the carriage of the sled and the base of the sled. For this reason, the user must manually create slack in the sled bag prior to fully attaching the catheter and beginning a pullback.

At least two different alternative configurations have been attempted for a two piece motor drive and sled pullback device, which only requires one sterile bag. Placing one bag is more desirable than two bags, because it requires less time and complexity in the set up. In the device presented in U.S. Pat. No. 6,309,358, the sterile bag has a locking interface. The bag is placed over the pullback device and the interface is locked to the pullback device. The catheter is then locked into the interface. Though there is only one bag covering the pullback device, the bag must still be bunched up by the user prior to the procedure. In addition, the catheter is not directly attached to the pullback device, so there is an additional attachment step. The device presented in U.S. Pat. No. 6,398,755, consists of a reusable motor drive and a disposable sterile sled. A single bag is placed over the motor drive and the sterile sled is attached to the motor drive by piercing the bag at the interface point. Because the carriage of the sled and the base of the sled are sterile, and do not need to be covered with a bag, there is no bunching up for the user to be concerned with. However, the user must now purchase not only the sterile bag but also a sterile sled for each procedure, increasing the cost per patient. In all of these devices, because the motor drive is separate from the sled, and thus needs to be attached, the motor drive is sometimes handled by itself, during which it is possible to drop and damage it. The device presented in U.S. Pat. No. 5,797,858 also allows for a single sterile bag. The required gearing for the longitudinal drive is a part of the sterile disposable catheter assembly, instead of being a part of the pullback device. The pullback device is covered with a single bag and the catheter is snapped in place. There is no bunching of the bag required. Another improvement with this device is that it does not have a separate motor drive and sled that need to be attached to each other. The only attachment step is the attachment of the catheter to the pullback device. However, the additional parts in the catheter increase its cost to manufacture. Thus, there exists a need for a single sterile bag that can enclose both the carriage for the motor drive and the sled of a catheter pullback device and expand as the carriage is translated along the sled.

SUMMARY OF THE INVENTION

This invention relates to a pullback device, catheter and sterile bag design that overcomes many of the drawbacks of the previous designs. The catheter requires no extra parts and there is only one sterile bag required, so the cost per patient is a minimum. The pullback device does not consist of a separate motor drive and sled that must be attached to each other. It is a single component device that need only be covered by a bag. The bag has built in pleats that allow for the longitudinal displacement of the moving portion of the pullback device in relation to the stationary portion, without requiring that the user bunch up the material. The bag also has an orifice through which the proximal connector of the catheter is slid, allowing the catheter to be connected directly to the motor drive, without risk of contamination. A simple partial turn of the catheter connector into the pullback device locks it in place. The catheter is configured with a rigid inner sheath to minimize the chance of kinking during use with the pullback device. The catheter also has a reinforced guidewire lumen to avoid tearing of the lumen by the guidewire.

BRIEF DESCRIPTION OF THE DRAWINGS

FIG. 4 is a detailed view of the distal end of the same IVUS catheter.

FIG. 4a is an orthogonal view of the same distal end, showing the drive shaft/transducer assembly inside.

DETAILED DESCRIPTION OF THE DRAWINGS

Figure 1:
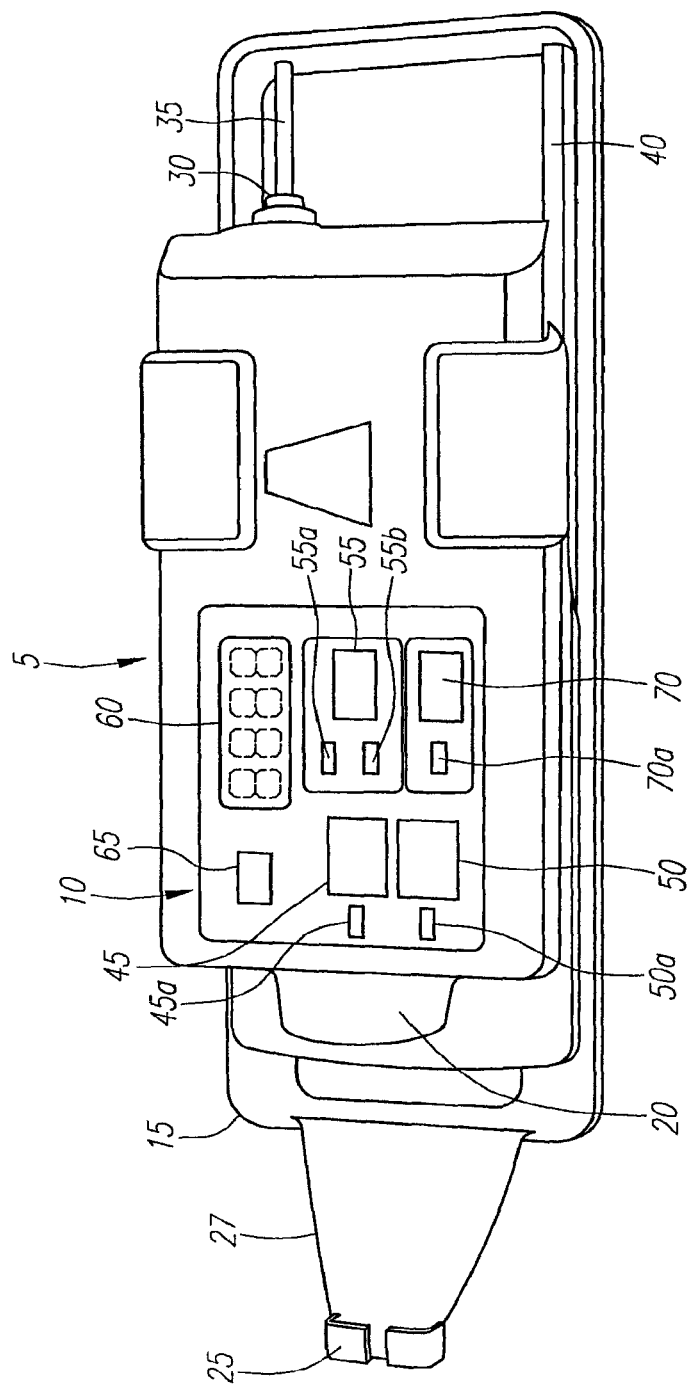
FIG. 1 illustrates a pullback device.

FIG. 1 shows a unitary pullback device 5 for moving an ultrasonic transducer 175 of an IVUS catheter 120 in the axial direction inside a blood vessel. The pullback device 5 consists of a motor drive 10 and a sled 15. The motor drive 10 and the sled 15 are permanently attached to each other, allowing the pullback device 5 to be handled, carried, stored and used without need to attach or detach the motor drive 10 and sled 15, and without the possibility of misplacing or damaging the motor drive 10. The pullback device 5 has two portions to which the IVUS catheter 120 is attached; they are a catheter interface 20 and an outer sheath clip 25. The motor drive includes a rotational motor (not shown), which serves to rotate the drive shaft 165 of the IVUS catheter 120. Power is delivered to the pullback device via a cable (not shown) that is attached to a cable input 30 on the motor drive 10. In addition, information is transferred to and from the pullback device via the same cable. During pullback, the motor drive 10 is moved longitudinally along the sled 15 over rod 40 and rack/rod 35. The motor drive 10 can be driven on rack/rod 35 by a pinion gear (not shown).

Figure 2:
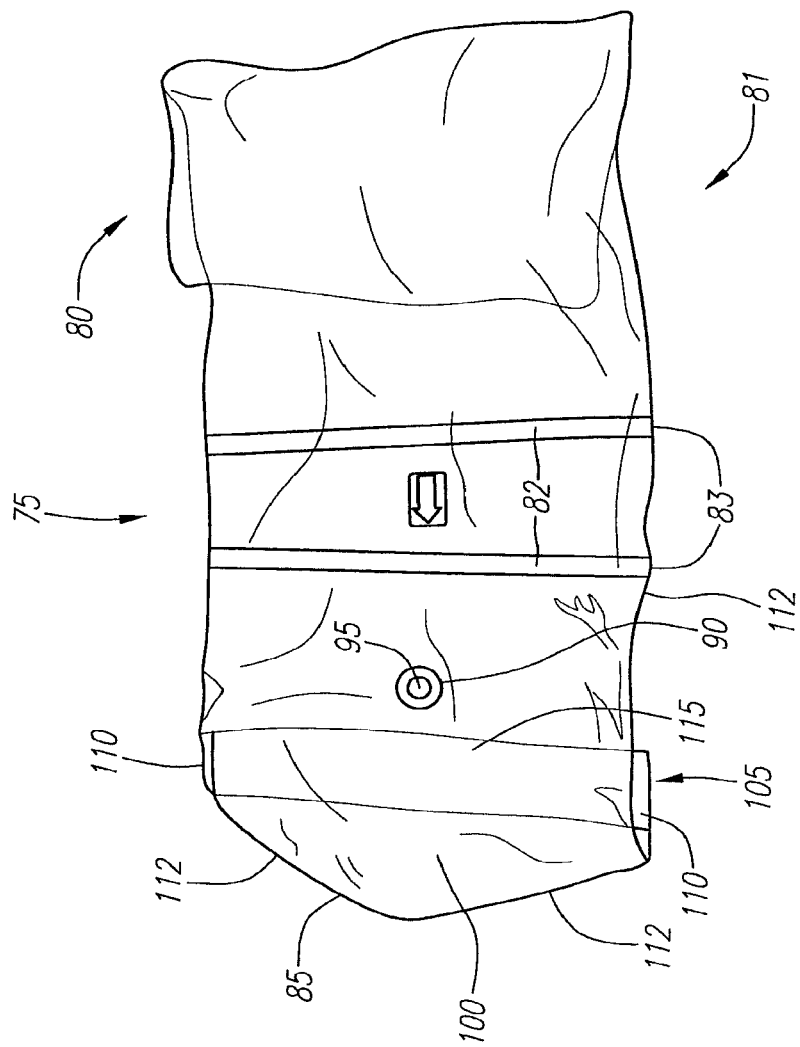
FIG. 2 illustrates a sterile bag with pleats and an orifice.

Turning now to FIG. 2, a sterile bag 75 is represented that serves to cover the pullback device 5 in order to maintain sterility during a sterile procedure. The sterile bag 75 includes a proximal end 80 having extendable folds that can be unfolded to cover the cable. The distal end 85 of the sterile bag 75 may include a clipping target area 100 for clipping the catheter to the outer sheath clip 25. A ring 90 having an orifice 95 may be located along the centerline of the sterile bag 75 and may be sized to allow passage of the very proximal end of the IVUS catheter 120. In between the clipping target area 100 and the ring 90 is a pleated section 105 that consist of folds 115 that are sealed on the side of the sterile bag 75 by multiple layer seals 110. The multiple layer seals 110 may be continuous with single layer seals 112 on the sides of the bag. The sterile bag 75 may also be attached to a sterile drape 81 by use of adhesive strips 82. As supplied to the user, the adhesive strips 82 may be covered by peelable adhesive strip covers 83. The sterile bag 75 is preferably constructed of polyethylene, but can also be constructed of polyester, nylon, polyvinyl chloride and other polymeric materials. The multiple layer seals 110 and single layer seals 112 may be made using a heat seal process in which the materials are melted together at the desired locations. Alternatively, adhesives or epoxies may be used.

Figure 3:
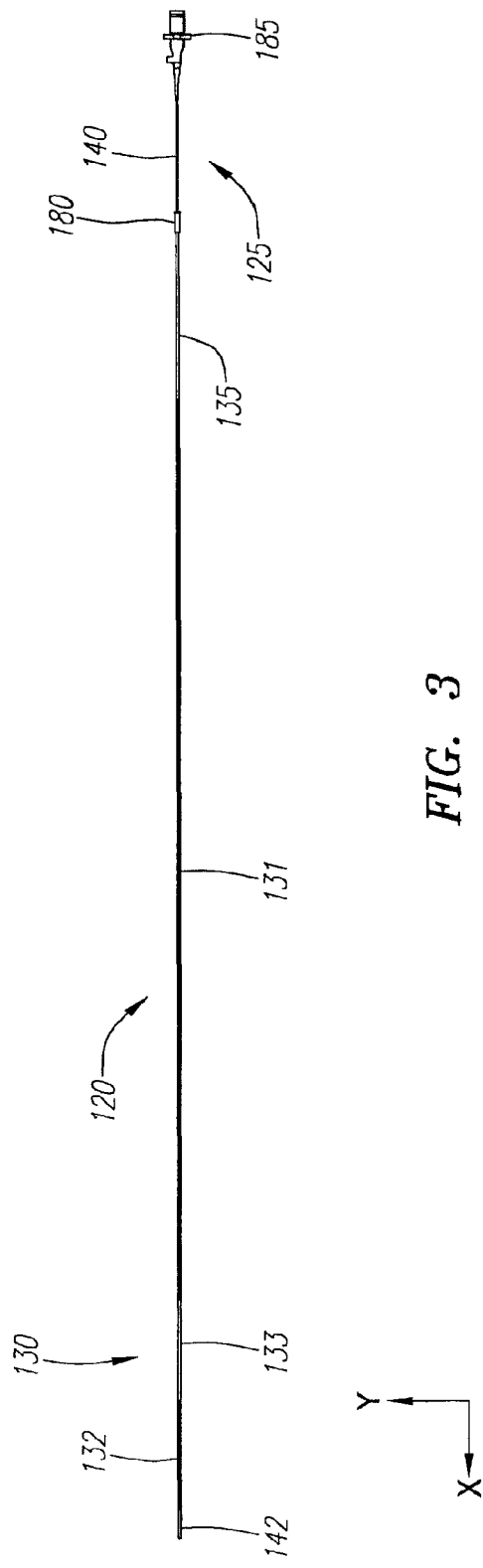
FIG. 3 illustrates an IVUS catheter for use with the sterile bag and pullback device.

FIG. 3 shows an IVUS catheter 120 for use with the pullback device 5 and sterile bag 75. The IVUS catheter 120 has a proximal end 125 and a distal end 130. The proximal end includes an outer sheath 135 and a telescoping inner sheath 140. The inner sheath is attached to a catheter connector 185. The outer sheath 135 is attached to a sheath hub 180. When the catheter connector 185 is translated axially in relation to the sheath hub 180, an ultrasonic transducer 175 inside the catheter is in turn translated. The inner sheath 140 is preferably made from PEEK (poly ether ether ketone) that makes for a very rigid tube that is resistant to kinking. The IVUS catheter 120 consists of a relatively long and stiff proximal catheter tubing 131 and a relatively flexible distal catheter tubing 132. The proximal catheter tubing 131 allows the catheter to be pushed with sufficient force, while the distal catheter tubing 132 allows smooth tracking through tortuous coronary vessels. In addition, an intermediate catheter tubing 133 can be bonded between the proximal catheter tubing 131 and the distal catheter tubing 132. This intermediate catheter tubing 133 preferably has a stiffness between that of the other two tubings, and allows for smooth motion of the catheter around the aortic arch and out the curved ends of guiding catheters. The IVUS catheter 120 also has a distal tip 142, which is tapered and has a small diameter, allowing it to more easily enter tortuous and stenosed coronary anatomy.

FIG. 4 shows more detail of the distal end 130 of the IVUS catheter 120. This distal end 130 is securely held to the rest of the IVUS catheter 120 with a tensile member 152, which can be constructed of stainless steel, Kevlar® (Dupont registered trademark) or other high tensile materials. A guidewire lumen 148 extends between a distal guidewire lumen opening 145 and a proximal guidewire lumen opening 150, and allows the catheter to be inserted and removed over a standard guidewire. The standard guidewire used in coronary applications has an outer diameter of 0.014". As shown in this preferred embodiment, this guidewire lumen 148 is relatively short, between 0.25 cm and 3 cm, preferably between 1.25 cm and 2 cm. A lumen reinforcement 155 is carried by the guidewire lumen 148. The lumen reinforcement 155 is preferably constructed of polyimide tubing or other high strength materials. The lumen reinforcement 155 typically has an inner diameter of 0.018" to 0.021" and a wall thickness of 0.001" to 0.003". The lumen reinforcement 155 has a typical length of 0.040" to 0.500". If during a procedure, the catheter is retracted and it causes the portion of guidewire exiting the proximal guidewire lumen opening 150 to loop, the lumen reinforcement 155 will assure that the guidewire lumen 148 will not tear. The distal tip 142 of the IVUS catheter 120 includes a radiopaque marker 160, which can be constructed of platinum, platinum/iridium, gold, or other radiodense materials. This marker allows the tip of the catheter to be visible on fluoroscopy. FIG. 4a shows more detail of the distal end 130 of the IVUS catheter 120. A drive shaft lumen 162 contains a rotatable drive shaft 165. At the distal end of the drive shaft is a housing 170 on which is attached an ultrasonic transducer 175.

Figure 5:
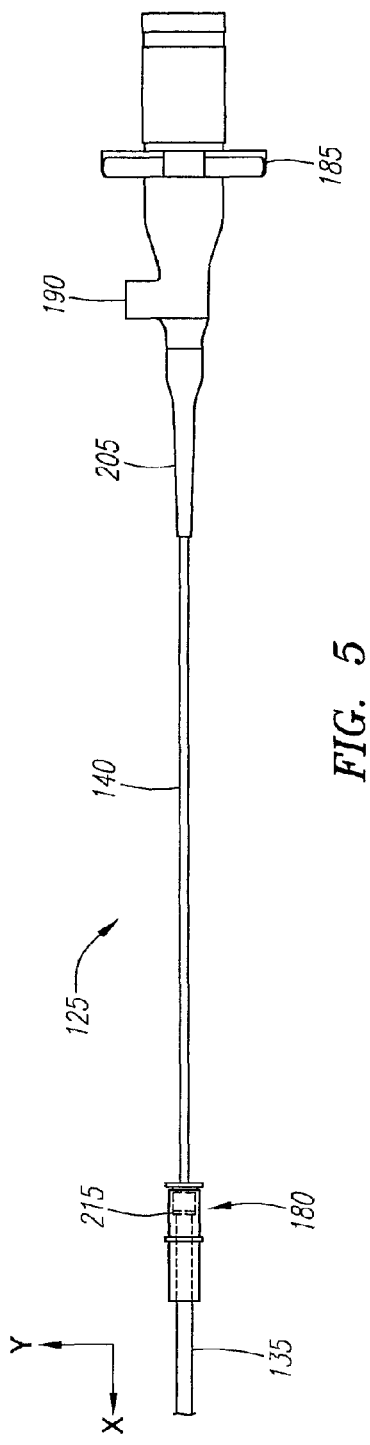
FIG. 5 is a detailed view of the proximal end of the same IVUS catheter.
Figure 5A:
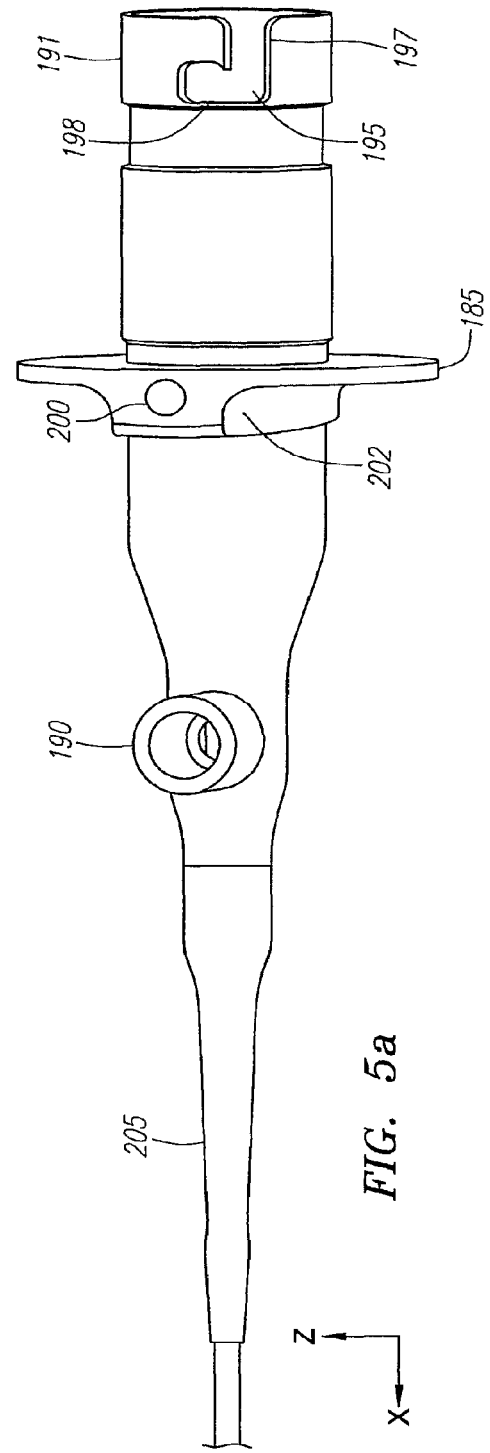
FIG. 5a is a detailed view of the catheter connector of the same IVUS catheter.

Turning now to FIGS. 5 and 5a, the proximal end 125 of the IVUS catheter 120 is shown. As previously described, the inner sheath 140 translates inside outer sheath 135. Fluid is sealed between the two sheaths by a seal 215 carried by the sheath hub 180. Catheter connector 185 contains a luer port 190 through which fluid can be injected into the two sheaths and through the drive shaft lumen 162. Catheter connector 185 includes an insertion surface 191 that may include one or more grooves 195. Catheter connector 185 may also include a gripping ridge 202 and an indicator 200. A strain relief 205 may help to keep the catheter from kinking when handled.

Figure 6:
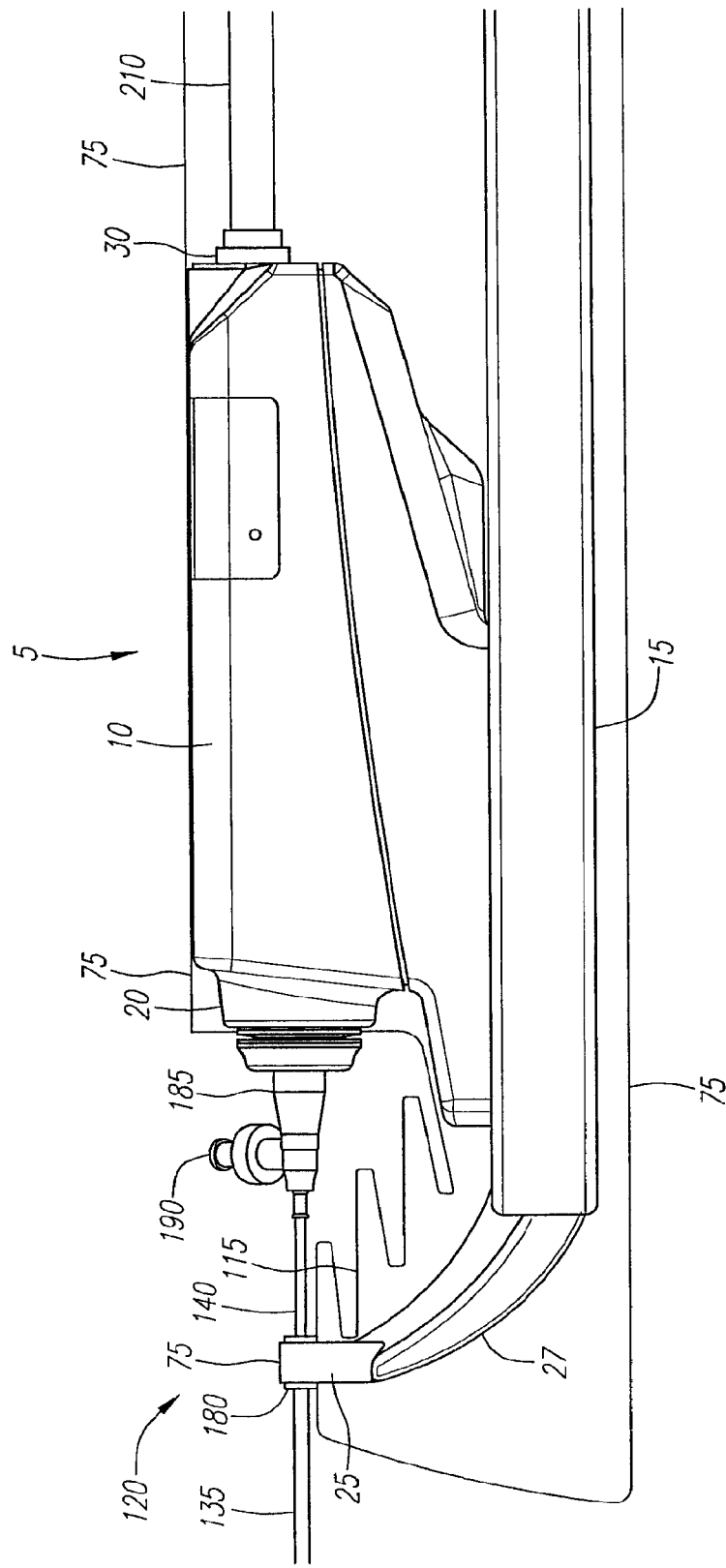
FIG. 6 is side view of the IVUS catheter attached to the pullback device and covered by the sterile bag, with a longitudinal section shown down the centerline of sterile bag.
Figure 6A:
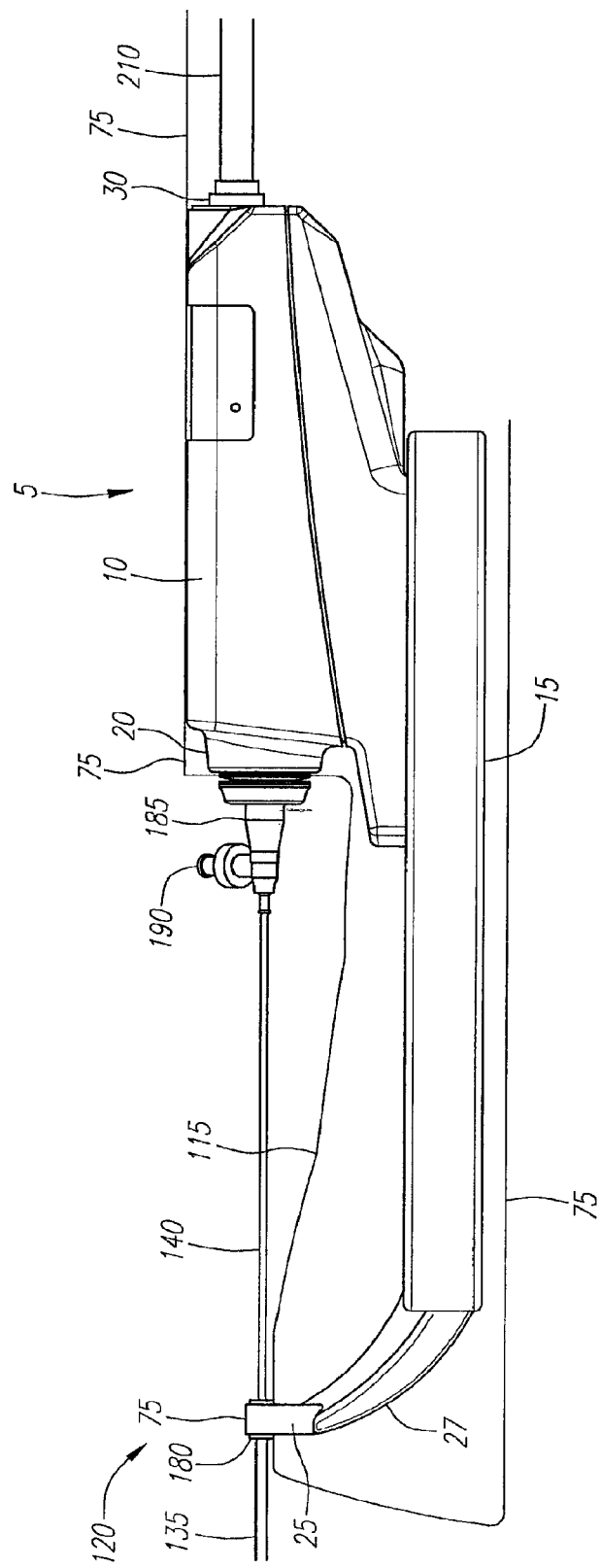
FIG. 6a is the same combined view as FIG. 6, but with the pullback device and catheter in fully retracted positions.

FIGS. 6 and 6a illustrate the pullback device 5 in place inside the sterile bag 75 with IVUS catheter 120 attached. In these figures the sterile bag 75 alone is cut away in a longitudinal section in order to show the condition of the folds at the centerline. As shown in FIG. 6, the folds 115 may be oriented so that each fold element steps down towards the right side of the figure. In this manner, the outer sheath clip 25 and support 27 of the sled 15 will not catch on the inwardly folded portions of the folds 115 as the pullback device is inserted into the sterile bag 75. In FIGS. 6 and 6a, cable 210 can be seen extending from cable input 30. FIG. 6 represents the configuration of the components at the beginning of a pullback, when the motor drive 10 is at the most distal location in relation to the sled 15. FIG. 6a, shows the components in the most retracted position, after a maximum length pullback, for example 15 cm. As seen in FIG. 6a, the folds 115 have been extended. The extra slack in the assembly due to the initial configuration of the folds 115 assures that no stress is placed upon the junction between the catheter connector 185/bag 75/catheter interface 20 or the junction between the sheath hub 180/bag 75/outer sheath clip 25, so that there is no slippage or tearing of the bag, and the connections stay connected.

Figure 7:
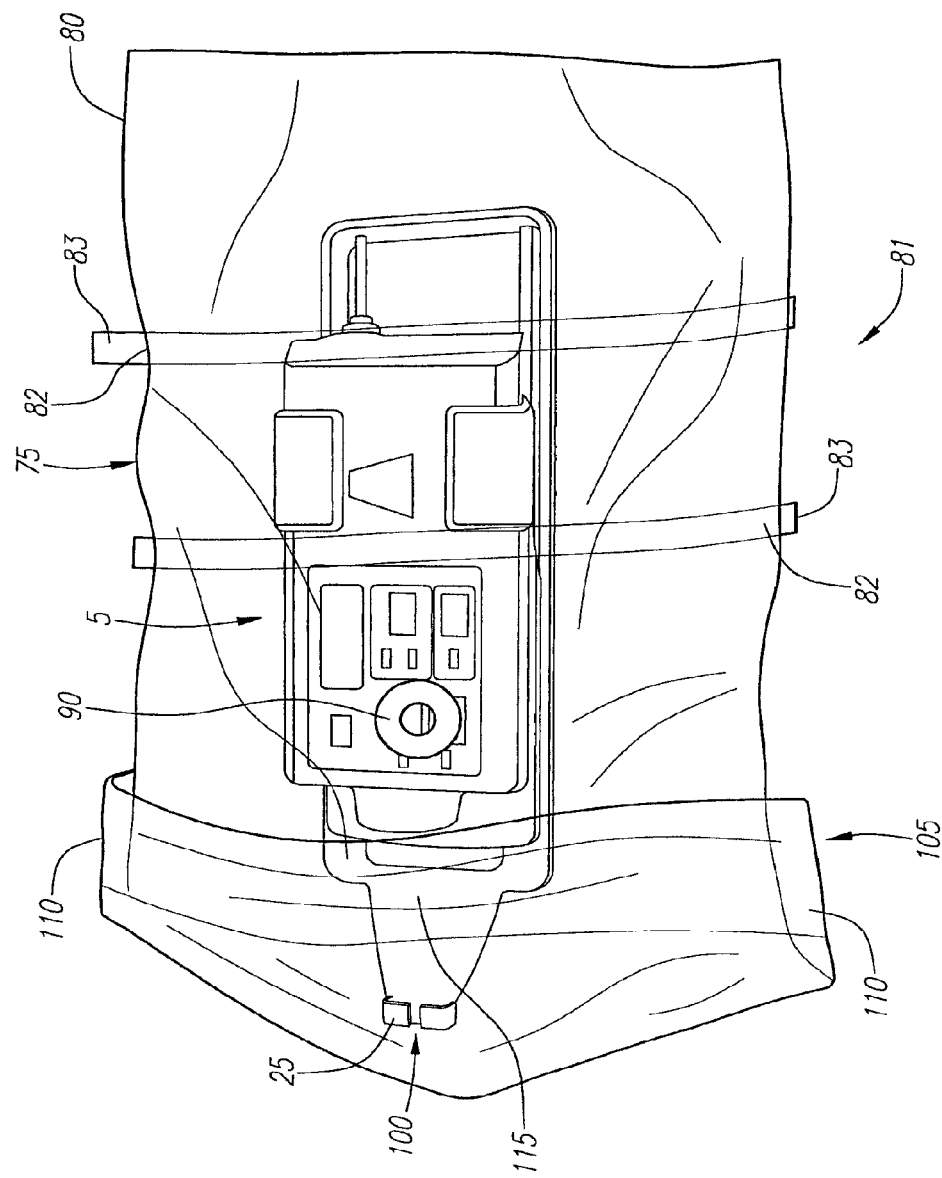
FIG. 7 illustrates the pullback device after initial placement in the sterile bag.
Figure 8:
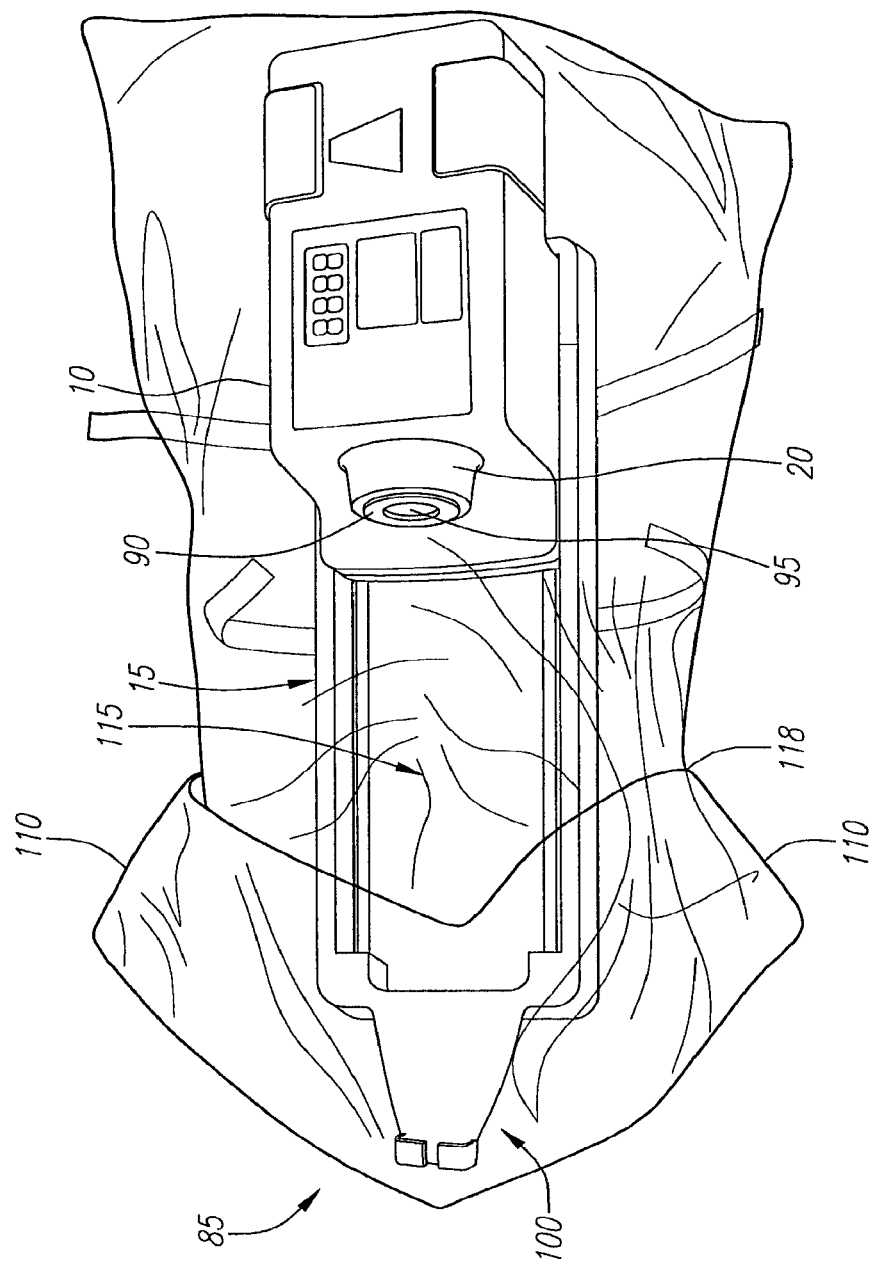
FIG. 8 illustrates the pullback device inside the sterile bag, with the motor drive of the pullback device retracted and the ring of the sterile bag inserted into the motor drive, the preferred configuration for catheter attachment.

FIGS. 7-19 show the steps required for setting up and using the pullback device 5 with the sterile bag 75 and IVUS catheter 120. FIG. 7 shows the pullback device after it has been inserted into the sterile bag. The outer sheath clip 25 has been inserted so that it passes the pleated section 105. The pullback device has been inserted sufficiently so that the clipping target area 100 of the sterile bag 75 aligns with the outer sheath clip 25 of the sled 15. The proximal end 80 of the sterile bag 75 has been unfolded so that it covers the cable (not shown), all the way past the end of the sterile field (for example the sterile drape 81). As shown in FIG. 8, after being placed in the sterile bag 75, the ring 90 of the sterile bag is inserted into the cavity of the catheter interface 20 of the motor drive 10. This effectively covers all of the motor drive with the sterile bag, except the portion where the sterile IVUS catheter 120 will be placed. A small removable barrier may be packaged over the orifice 95 of the ring 90 in order to better maintain sterility, until the catheter connector is attached. The pullback device 5 is then manipulated so that the motor drive 10 is retracted completely in relation to the sled 15. This is the ideal position for the attachment of the IVUS catheter 120 because the IVUS catheter 120 will be in the ideal flushing configuration and the additional space between the catheter interface 20 and the outer sheath clip 25 assures that the catheter will not be easily kinked during attachment. With the motor drive 10 in the most retracted position, the folds 115 of the pleated section 105 are for the most part extended. Also, this rearrangement of bag material creates a waist 118 in the sterile bag 75.

Figure 9:
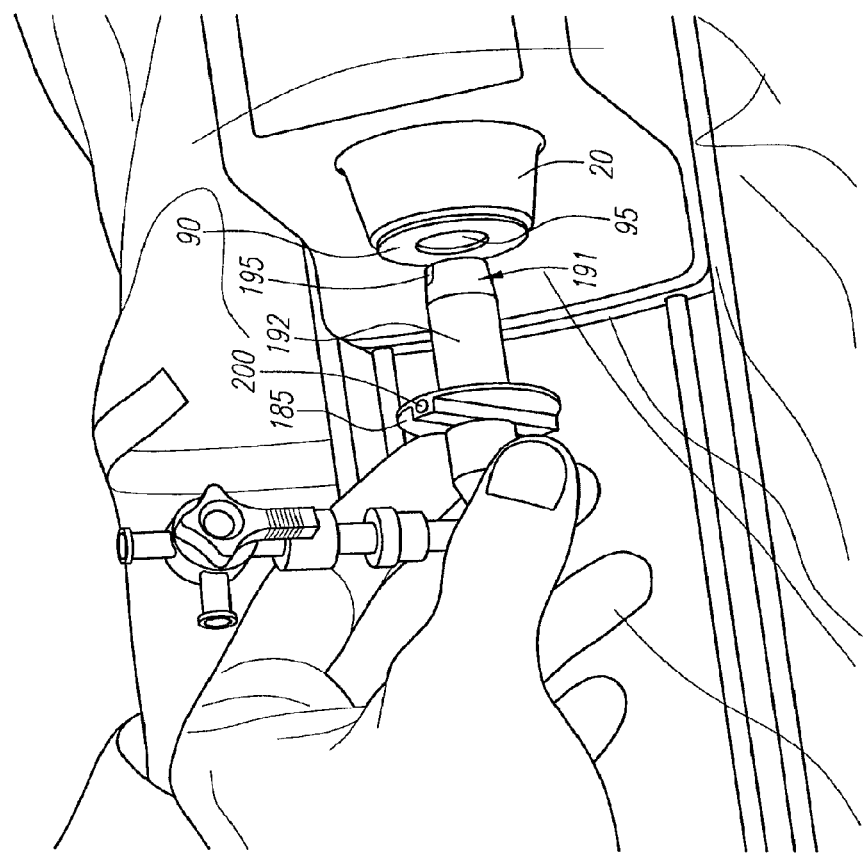
FIG. 9 illustrates the IVUS catheter being inserted into the motor drive of the pullback device through the orifice in the sterile bag.
Figure 10:
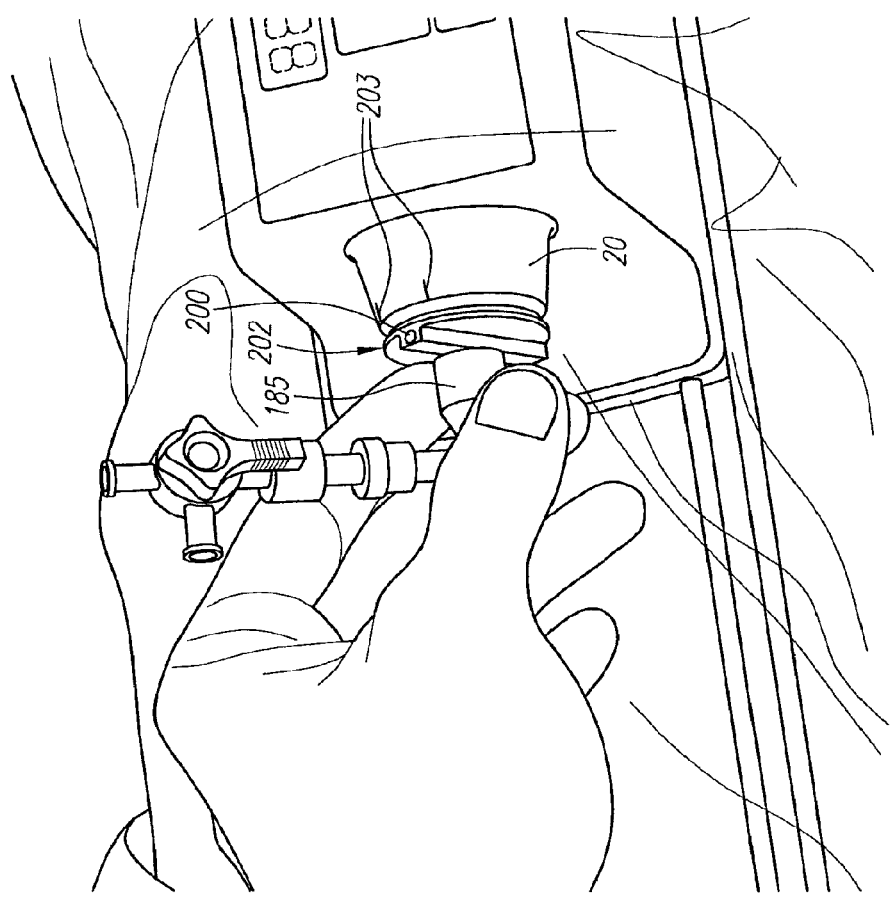
FIG. 10 illustrates the IVUS catheter being locked onto the pullback device.
Figure 11:
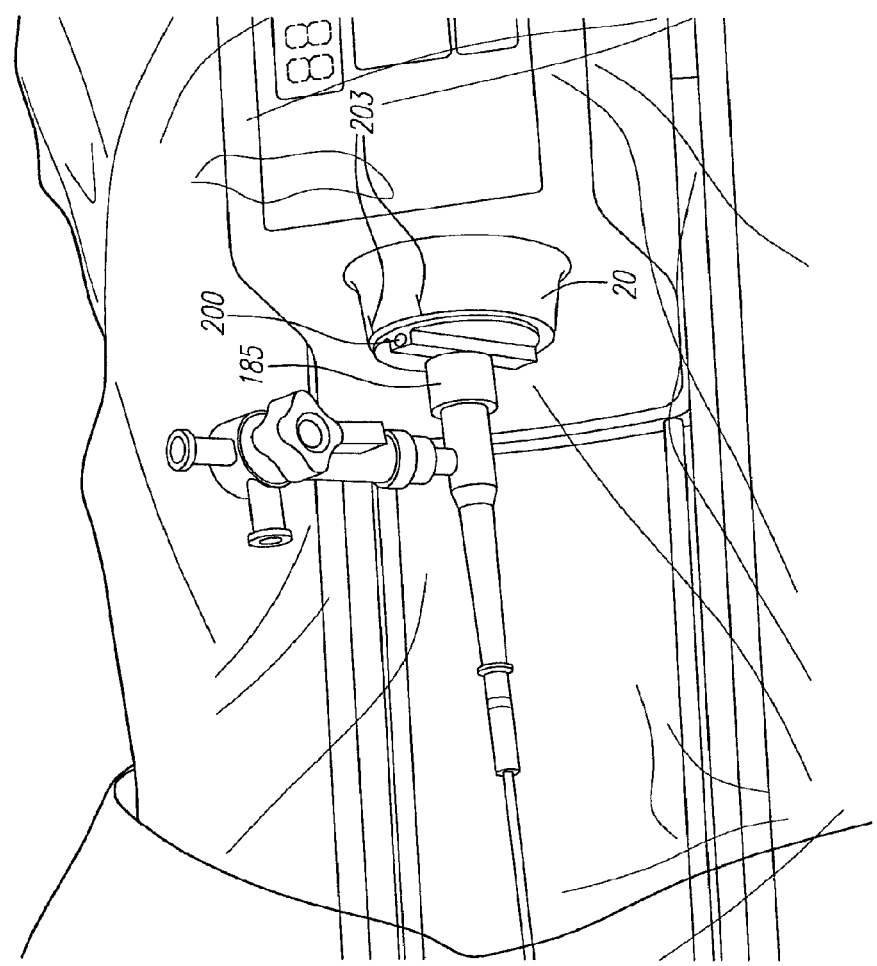
FIG. 11 illustrates the IVUS catheter in its locked state.

As shown in FIG. 9 the catheter connector 185 may be inserted of through the orifice 95 of the ring 95 of the sterile bag 75 and into the cavity of the catheter interface 20. The proximal end 192 of the connector includes an insertion surface 191 that may be sized to fit through the orifice 95 of the ring 90 with a slight clearance. This assures a closed sterile barrier after the catheter connector 185 is fully inserted and attached. An indicator 200 on catheter connector 185 may serve as an aid to the user to allow that the connector be inserted at the correct circumferential orientation. For example, in this case, the indicator is inserted at 60° off of vertical. This allows groove 195 to slide over an internal guide (not shown) that is located inside the cavity of the catheter interface 20. FIG. 5a shows that the groove 195 in the catheter connector 185 is made up of an axial groove 197 and a circumferential groove 198. When the catheter connector is inserted into the cavity of the catheter interface 20, the internal guide fits into the axial groove 197 of the groove 195 until the catheter connector 185 bottoms out. The catheter connector is then turned 30° clockwise to lock it into place, as shown in FIGS. 10 and 11. As shown in FIG. 10, the catheter connector 185 may be grasped by the gripping ridge 202 so that it can be turned. The circumferential groove 198 will then slide along the internal guide until the catheter connector reaches its locked position, as seen in FIG. 11. This locked position may be achieved by an internal locking mechanism, such as a spring loaded lock. Alternatively, there may be one or more markings 203 on the catheter interface 20 that allow the alignment of the indicator 200 of the catheter connector 185 at both the insertion orientation and the locked orientation. When the catheter connector 185 is locked in place to the catheter interface 20 of the motor drive 10, there is a mechanical and electrical connection to the drive shaft 165 of the IVUS catheter 120 and a mechanical and electrical connection to the catheter connector 185. The mechanical connection to the catheter connector 185 keeps it circumferentially static, while the mechanical connection to the drive shaft 165 allows it to be rotated with respect to the catheter connector and catheter tubing, and thus, with respect to the blood vessel. The electrical connection to the drive shaft 165 allows a signal to be sent to the transducer 175, causing it to vibrate, and allows a signal to be received from the transducer 175, after it responds to echoes.

Figure 12:
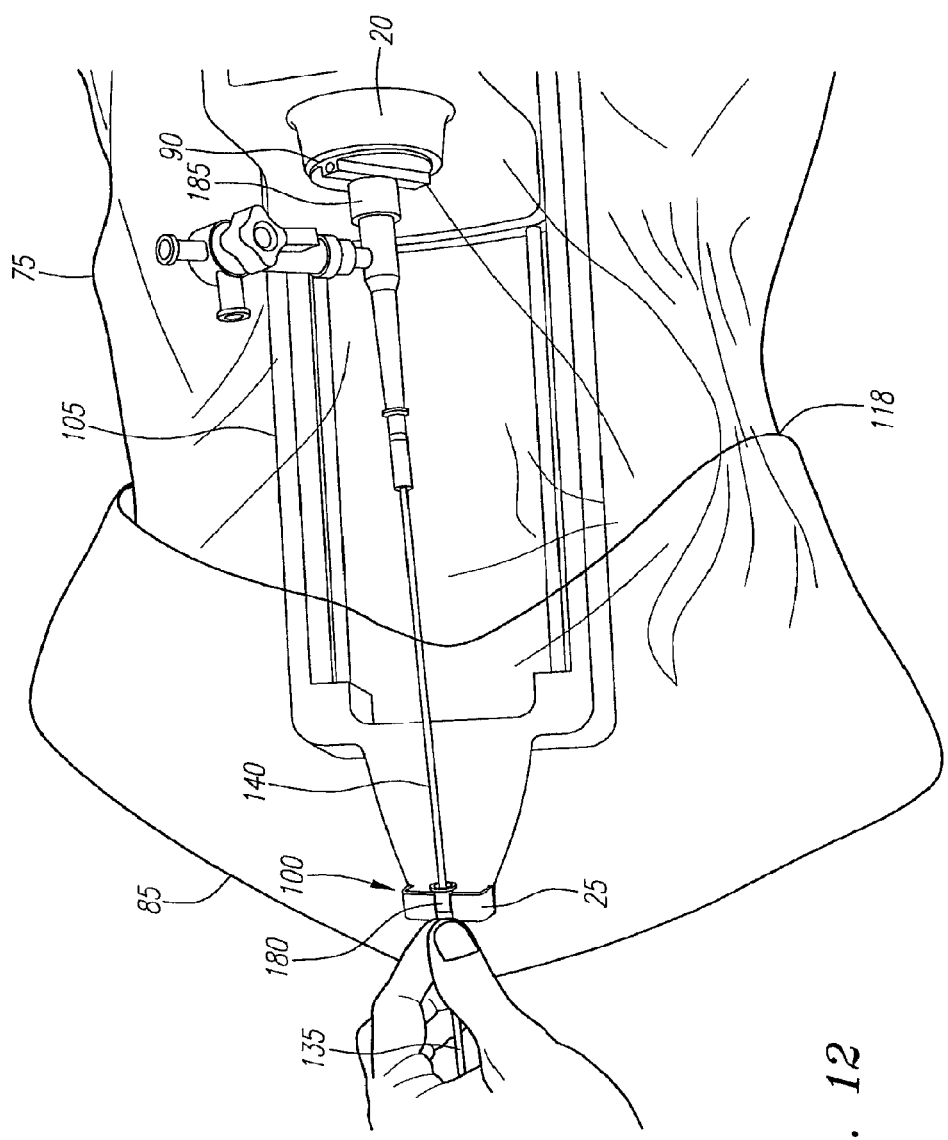
FIG. 12 illustrates the outer sheath of the IVUS catheter being attached to the outer sheath clip of the pullback device.
Figure 13:
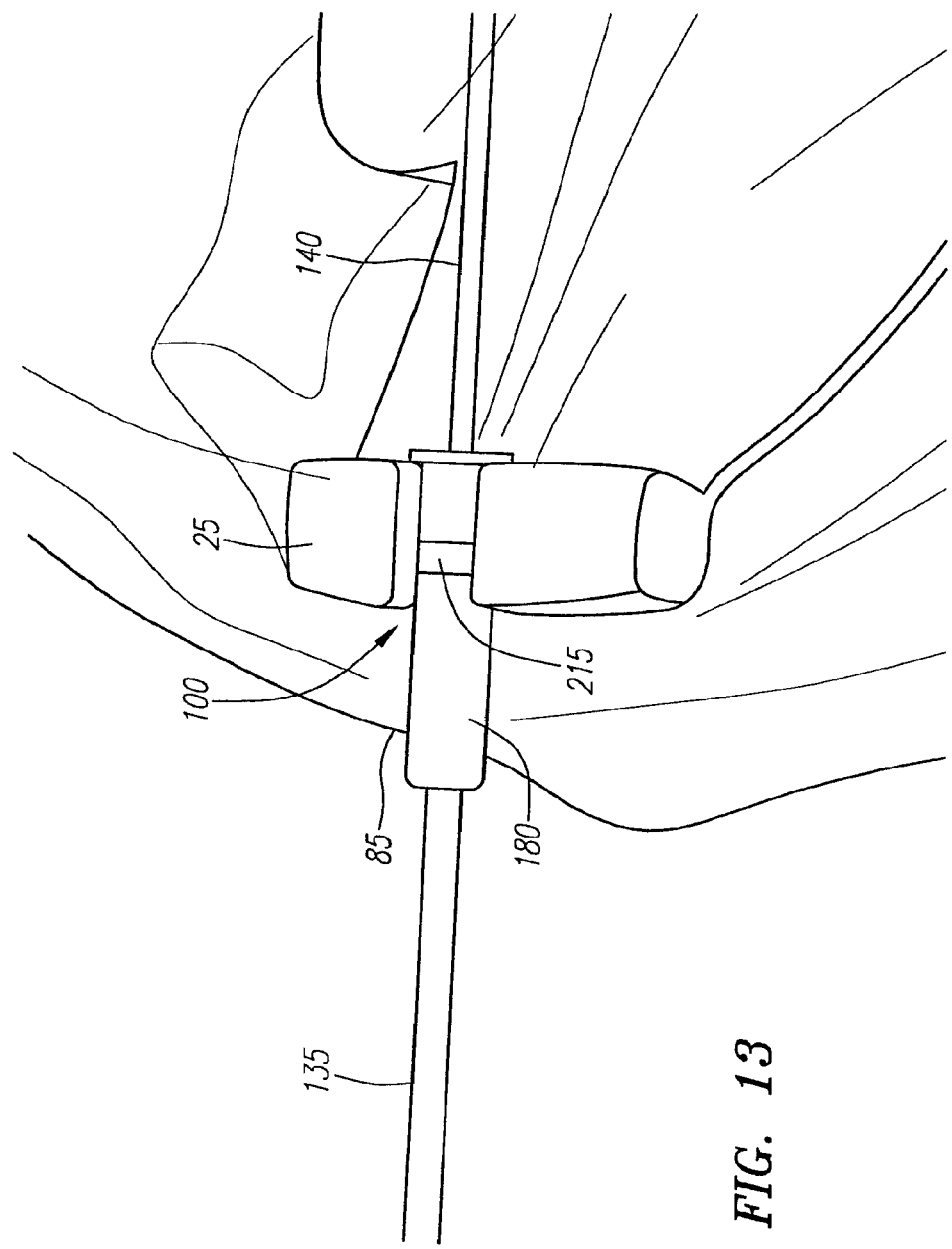
FIG. 13 illustrates a close-up of the sheath hub of the outer sheath of the IVUS catheter secured to the outer sheath clip of the pullback device.

As seen in FIGS. 12 and 13, after the catheter connector 185 may be locked into place on the catheter interface 20 of the motor drive 10 while the outer sheath of the 135 may be secured to the sled 15 by snapping the sheath hub 180 to the outer sheath clip 25. The clipping target area 100 of the sterile bag 75 may be located between the sheath hub 180 and the outer sheath clip 25 when they are secured together. The distal end 85 of the sterile bag 75 and the ring 90 of the sterile bag 75 are therefore secured to the sled 15 and the motor drive 10 respectively. Back and forth longitudinal translation will not be hampered, because the pleated section 105 of the sterile bag 75 allows for sufficient slack. Also, the sterile bag 75 is able to form a waist 118, when the motor drive is pulled back, also allowing for the necessary slack.

Figure 14:
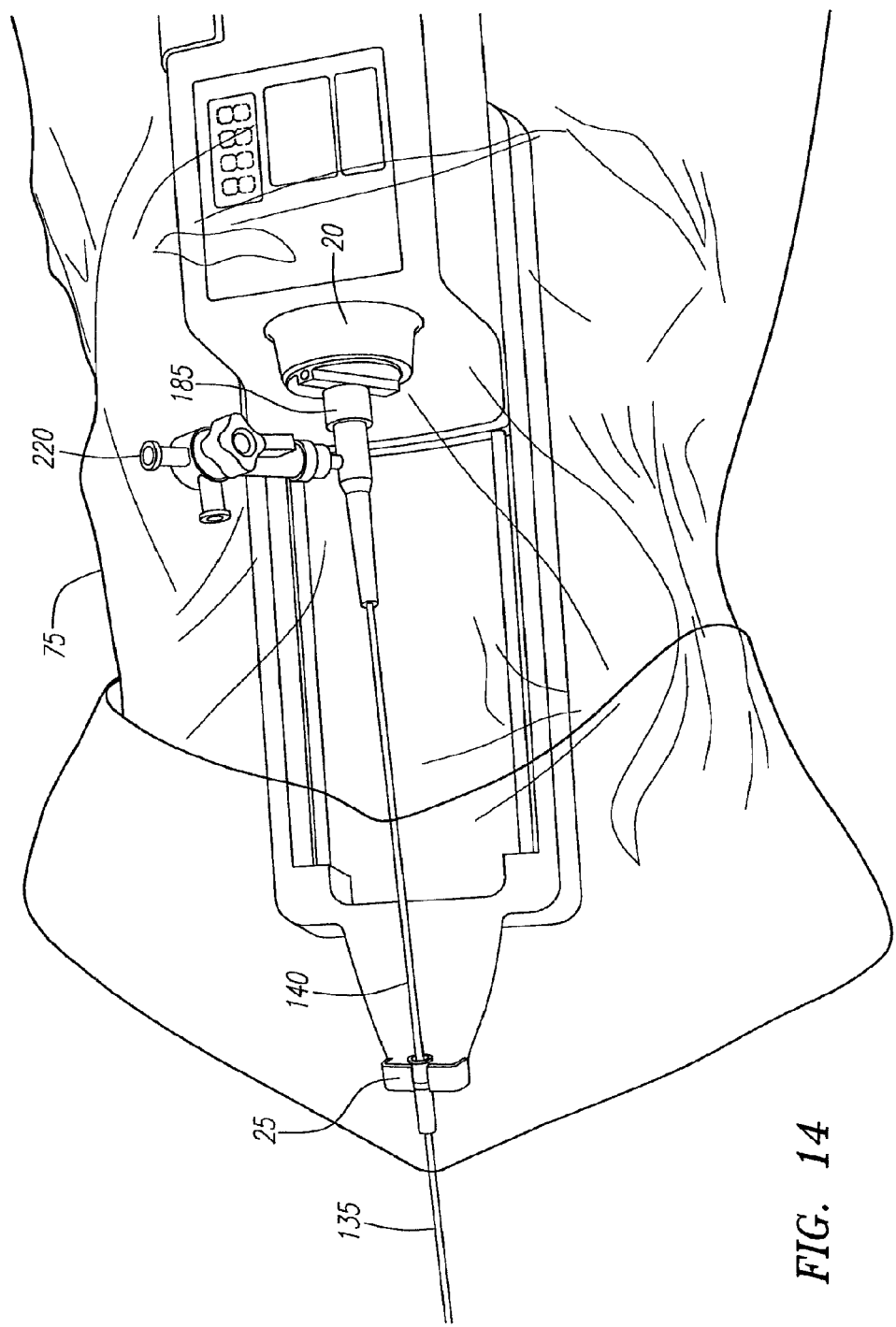
FIG. 14 illustrates the IVUS catheter, pullback device and sterile bag in the attached and fully retracted configuration, ready for catheter priming.
Figure 15:
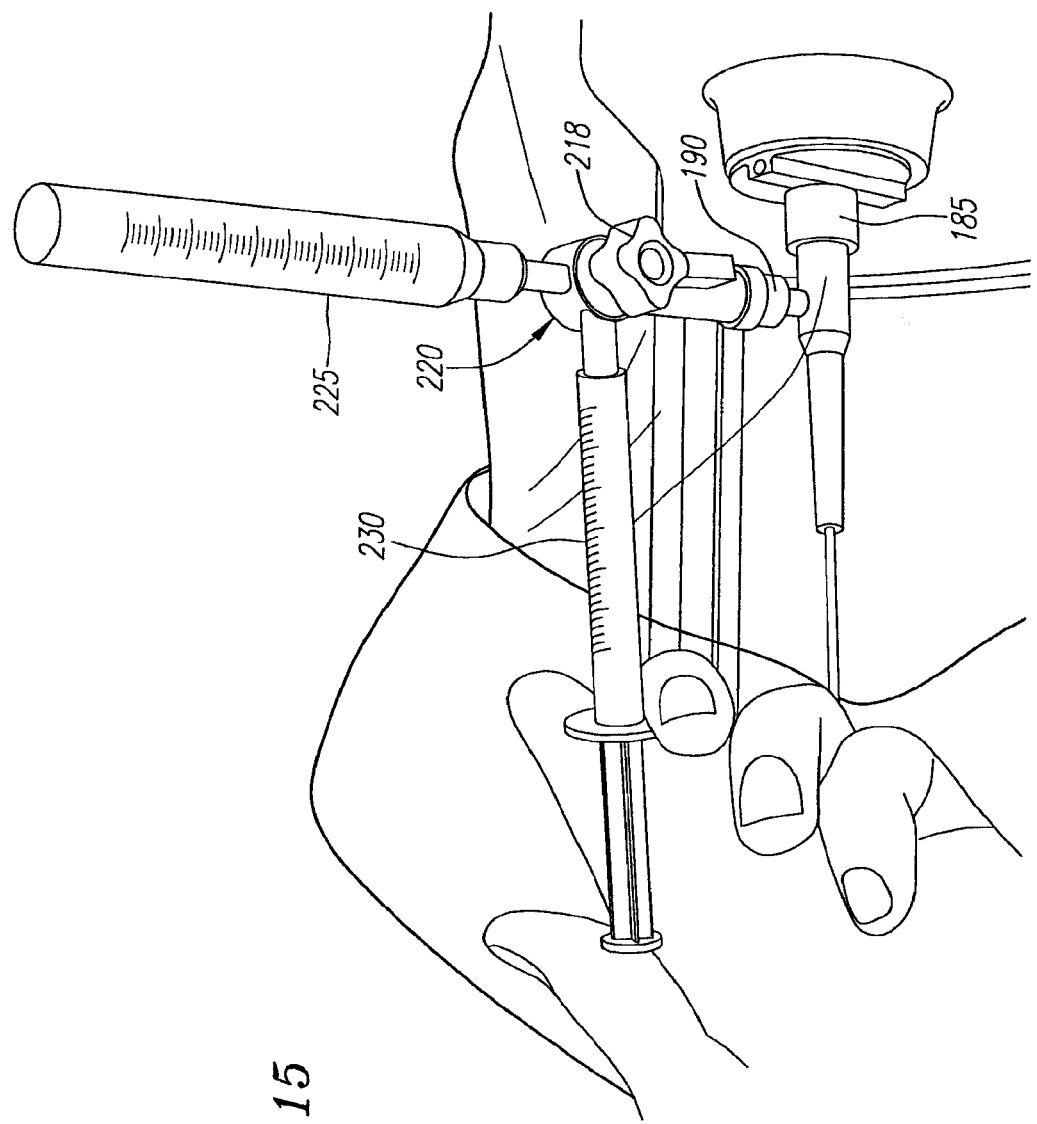
FIG. 15 illustrates the catheter priming step.

FIG. 14 shows the assembled components in the desired position for priming the drive shaft lumen 162 of the IVUS catheter 120. The drive shaft lumen 162 is primed in order to remove all air from the system. Air does not have a good matching acoustic impedance with the transducer material, and therefore is typically replaced by priming with sterile, heparinized saline. By priming in the position shown in FIG. 14, the catheter lumen is filled at its extended configuration at which it has a maximum volume Therefore, air will not enter when the motor drive is advanced to the distal starting position. As seen in FIG. 15, a stopcock 220 is attached to the luer 190 of the catheter connector 185. The stopcock 220 pictured is a three-way stopcock, and allows for the attachment of two different syringes, a small bore syringe 230 and a large bore syringe 225. The valve 218 of the stopcock 220 can be selectively turned so that the small bore syringe 230 can be fed from the large bore syringe 225. The valve 218 can then be turned (as shown) so that the small bore syringe 230 can be used to inject sterile heparinized saline through the drive shaft lumen 162 of the IVUS catheter 120, purging it of all air. The valve 218 can then be closed, to maintain the primed condition. This is shown in FIG. 16.

Figure 16:
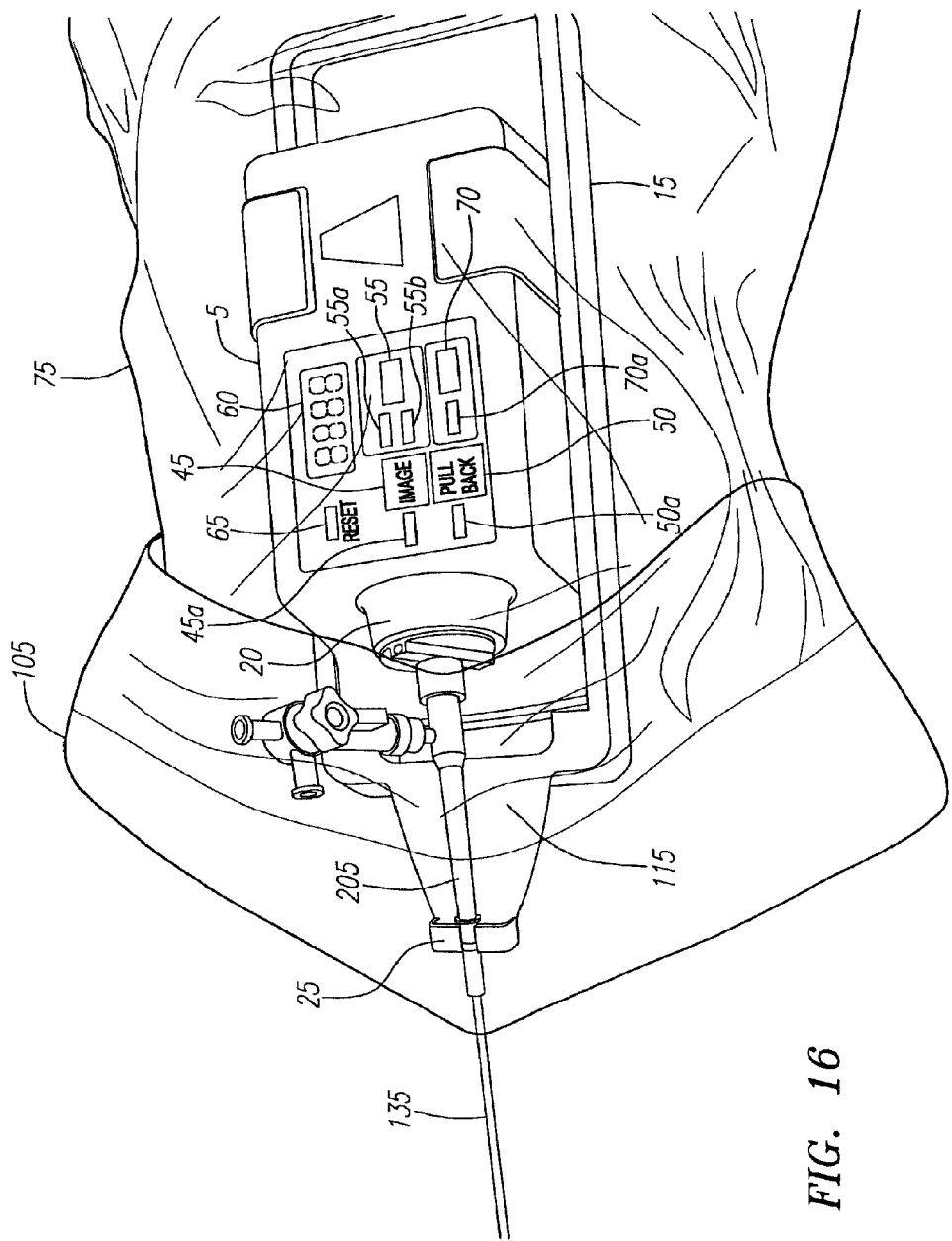
FIG. 16 illustrates the fully advanced configuration, after catheter priming and prior to the start of catheter pullback.

After priming is completed, the motor drive 10 is returned to its distal most position, as seen in FIG. 16. The sterile bag 75 returns to a configuration close to its original configuration. The folds 115 reappear in the pleated section 105 and the waist 118 disappears. Due to the clarity of the sterile bag material as well as its thin wall, it is easy to operate the different buttons and visualize the different displays on the motor drive 10. When image button 45 is pressed it causes the motor drive motor to operate, in turn rotating the drive shaft 165. It also begins the send and receive operation of the ultrasonic transducer 175. When image button is activated, image indicator 45a illuminates. When the image button 45 is pressed again, the drive shaft 165 stops rotating, the ultrasonic transducer 175 stops obtaining data and the image indicator 45a turns off. While the pullback device 5 is actively imaging, a manual pullback can be performed by pressing the manual pullback select button 70. When this button is depressed and manual pullback is selected, the manual pullback indicator 70a illuminates. The motor drive may then be moved by hand to the desired locations and pulled back in any desired speed. At the different longitudinal locations, the longitudinal displacement display 60 indicates the longitudinal displacement, for example 1.5 mm from the starting position. At any point along the displacement, the longitudinal displacement display 60 can be reset to 0.0 mm by pressing the longitudinal displacement reset button 65. Alternatively, the inner sheath 140 may be constructed with stripes, for example every 0.5 cm, to allow the user to get a quick estimate of longitudinal displacement. This can be effective for quickly choosing the desired length of stent to use to treat an atherosclerotic lesion.

If alternatively, an automatic pullback is desired, the automatic pullback button 55 is pressed, one time for a desired pullback speed of 0.5 mm per second and two times for a desired pullback speed of 1.0 mm per second. Speed indicator lights 55a and 55b illuminate when the speeds of 0.5 mm per second and 1.0 mm per second are selected, respectively. The longitudinal displacement display 60 and longitudinal displacement reset button 65 work in the same manner in an automatic pullback as they did during a manual pullback. An additional button (not shown) on the pullback device is known as a book mark button. This book mark button can be pressed at any time during the pullback, and the corresponding longitudinal location is recorded as a point of interest in the record of the pullback. For example, a bookmark may be pressed at the distal end of a stent, or the proximal end of a stent or in the middle of a lesion. This allows a physician to go directly to the areas of interest when reviewing recorded files of the procedure.

Figure 17:
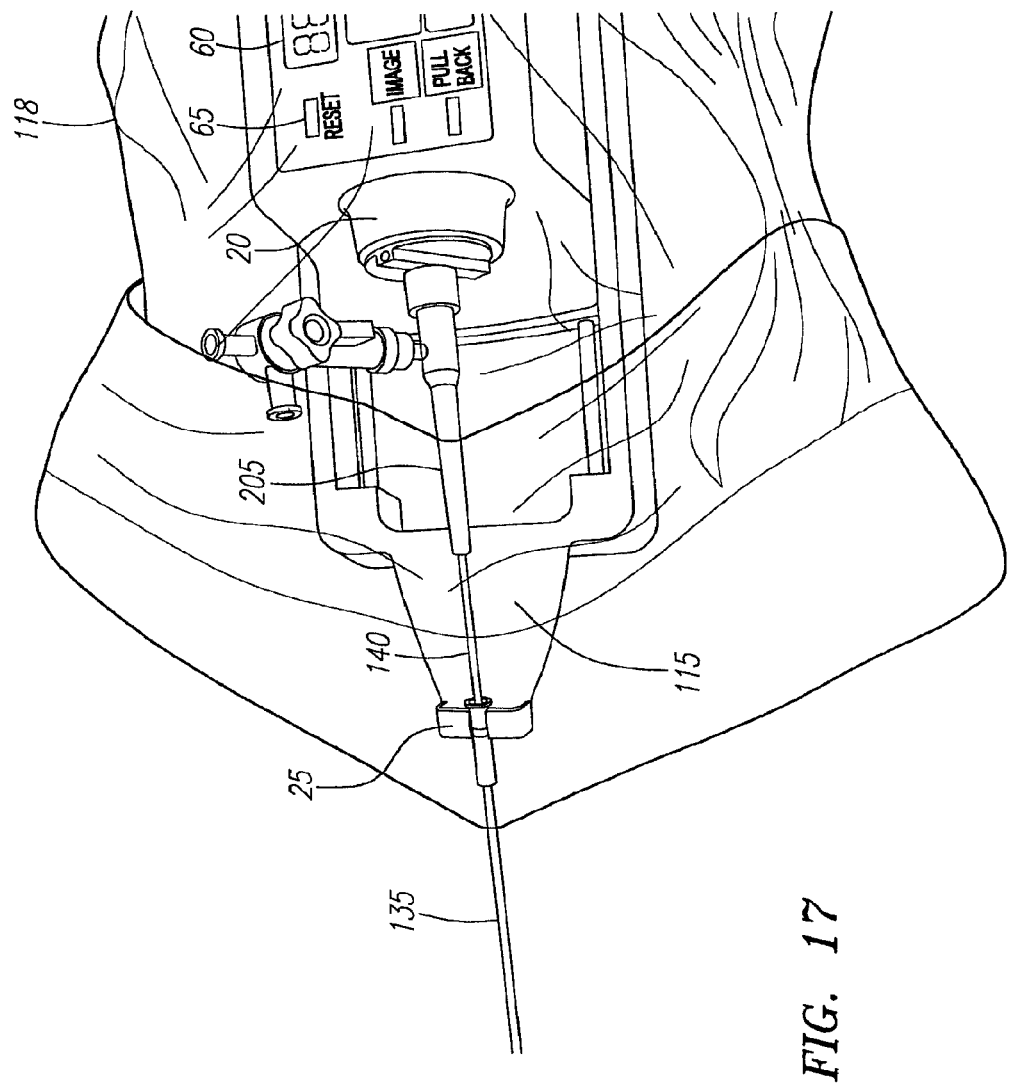
FIG. 17 illustrates the IVUS catheter/pullback device/sterile bag system after approximately 5 cm of pullback.
Figure 18:
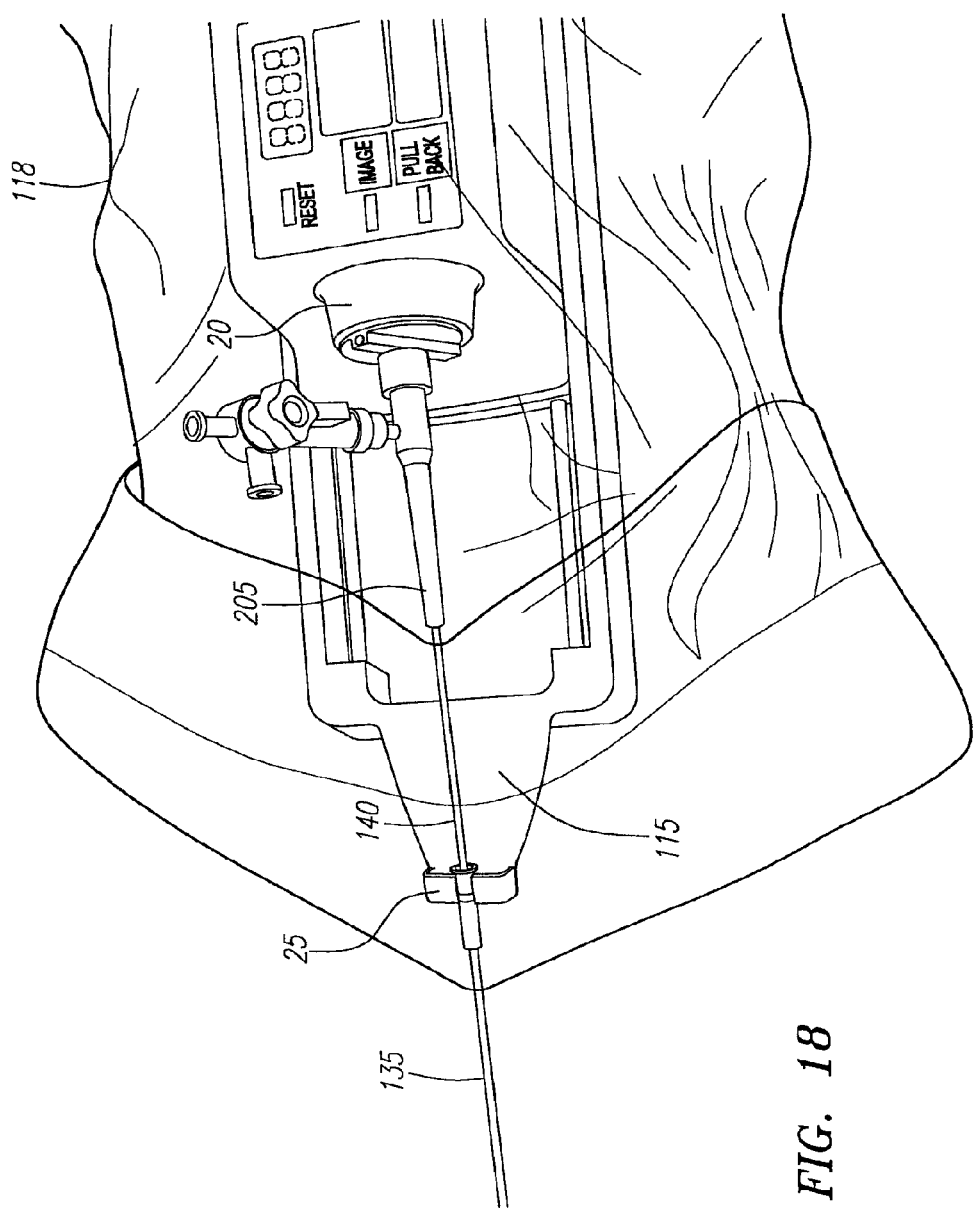
FIG. 18 illustrates the IVUS catheter/pullback device/sterile bag system after approximately 8 cm of pullback.
Figure 19:
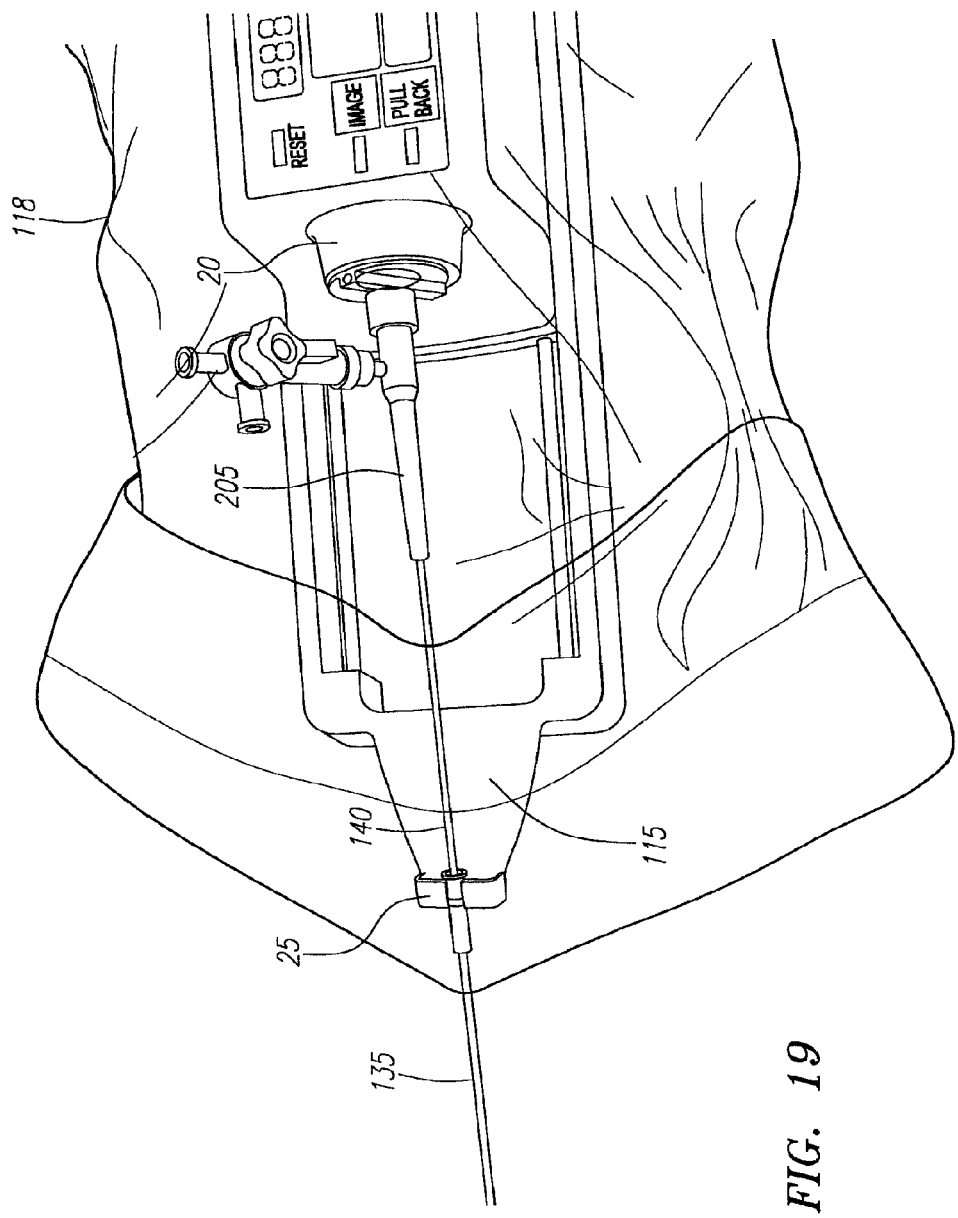
FIG. 19 illustrates the IVUS catheter/pullback device/sterile bag system after approximately 13 cm of pullback.

FIGS. 17-19 show the components of the system in several different positions along the course of a single pullback. FIG. 17 shows the components after 5 cm of pullback have been completed. There are still pronounced folds 115, and a waist 118 is just beginning to appear in the sterile bag 75. In FIG. 18, after 8 cm of pullback, there are fewer folds 115, and the waist 118 is becoming more pronounced. In FIG. 19, after 12 cm of pullback, there are only a few small folds 115 visible in the centerline of the sterile bag 75, and the waist 118 is very pronounced.

This invention is also applicable to other types of IVUS catheters, such as phased array IVUS catheters that do not have a rotating shaft, or rotating IVUS catheters that do not have an inner and outer sheath arrangement. In these applications, the entire catheter is pulled back in relation to the blood vessel. In this case, the outer sheath clip 25 may instead be used to hold the hemostatic valve or guiding catheter. Alternatively, it may not be used at all.

In addition to the bag configuration presented in this patent, an alternative bag configuration may contain a longitudinal slit down the center of the bag at the proximal end. This slit allows the pullback device to be lowered into place in the bag, instead of inserted horizontally. The slit may contain an adhesive or zip locking closure, in order to then close around the pullback device and thus maintain sterility. In addition, this alternative embodiment or the original embodiment is constructed of a short bag, in cases where the pullback device does not require a cable (for example, in a device having a battery). In this embodiment, the proximal end of the bag has an envelope-like adhesive seal for securely closing the proximal end of the bag over the proximal end of the pullback device.

What is claimed is:

1. A method of providing a sterile field for an intravascular procedure, comprising:
    providing an elongate bag having a distal end, a proximal end, and a chamber extending therebetween, the chamber sized to contain a catheter pullback device having a motor drive and a sled, the motor drive being translatable along a longitudinal axis of the sled during use, wherein the elongate bag further comprises:
        an upper sheet and a lower sheet, the lower sheet defining a plane;
        a plurality of pleats integrated near the distal end of the bag, the plurality of pleats being a series of folds only in the upper sheet near the distal end of the bag, each fold of the series of folds in the upper sheet laying in a plane that is generally parallel to the plane defined by the lower sheet, the plurality of pleats being expandable to facilitate expansion of the elongate bag to accommodate translation of the motor drive along the sled; and
        an orifice located proximally to the pleats and sized to allow passage of at least a portion of a catheter into the chamber of the bag in a direction parallel to the longitudinal axis; and
    positioning a catheter pullback device within the chamber of the elongate bag such that plane defined by the lower sheet extends parallel to the longitudinal axis.

2. The method of claim 1, wherein the provided elongate bag further comprises at least one fold extending from the proximal end that can be unfolded to cover a cable extending from the pullback device.

3. The method of claim 1, wherein the each fold in the series of folds of the provided elongate bag is offset proximally relative to the immediately preceding fold.

4. The method of claim 1, wherein the provided elongate bag is made of a material selected from a group consisting of polyethylene, polyester, nylon, polyvinyl chloride, or other polymeric materials.

5. The method of claim 4, wherein the provided elongate bag is made of polyethylene.

6. The method of claim 1, wherein the orifice of the provided elongate bag comprises a hollow ring.

7. The method of claim 1, further comprising: causing the motor drive being to translate along a longitudinal axis of the sled in a first direction thereby causing the pleats to expand.

8. The method of claim 7, further comprising: causing the motor drive being to translate along a longitudinal axis of the sled in a second direction opposite the first direction thereby causing the pleats to contract.

9. The method of claim 1, further comprising: causing the motor drive being to translate along a longitudinal axis of the sled in a first direction thereby causing the pleats to contract.

10. The method of claim 1, further comprising: coupling a catheter to the catheter pullback device positioned within the chamber of the elongate bag.

11. The method of claim 10, wherein the catheter is an imaging catheter.

12. The method of claim 11, wherein the catheter is an intravascular ultrasound (IVUS) catheter.

13. The method of claim 12, wherein the IVUS catheter is a rotational IVUS catheter.

14. The method of claim 12, wherein the IVUS catheter is a phased array IVUS catheter.

15. The method of claim 10, wherein coupling the catheter to the catheter pullback device includes introducing a catheter connector through the orifice of the elongate bag.

16. The method of claim 1, wherein the elongate bag further includes a longitudinal slit at the proximal end.

17. The method of claim 16, wherein positioning the catheter pullback device within the chamber of the elongate bag includes vertically lowering the catheter pullback device into the elongate bag through the longitudinal slit.

18. The method of claim 16, wherein the longitudinal slit includes a closure mechanism.

19. The method of claim 18, wherein the closure mechanism includes at least one of an adhesive and a zip lock.

20. The method of claim 1, wherein positioning the catheter pullback device within the chamber of the elongate bag includes horizontally inserting the catheter pullback device into the elongate bag.

* * * * *